United States Patent [19]

Dougherty et al.

[11] Patent Number: 4,968,715

[45] Date of Patent: Nov. 6, 1990

[54] USE OF PURIFIED HEMATOPORPHYRIN TRIMERS IN PHOTODYNAMIC THERAPY

[75] Inventors: Thomas J. Dougherty, Grand Island; Ravindra K. Pandey, Buffalo, both of N.Y.

[73] Assignee: Health Research, Inc., Buffalo, N.Y.

[21] Appl. No.: 343,865

[22] Filed: Apr. 26, 1989

Related U.S. Application Data

[63] Continuation-in-part of Ser. No. 215,592, Jul. 6, 1988.

[51] Int. Cl.$^5$ .............................................. A61K 31/40
[52] U.S. Cl. .................................... 514/410; 540/145
[58] Field of Search ........................... 540/145; 514/410

[56] References Cited

U.S. PATENT DOCUMENTS 4,649,151  3/1987  Dougherty et al. ................ 540/145

OTHER PUBLICATIONS

Scourides et al., Cancer Res (1987), 47:3439–3445.
Dougherty et al., Adv. Exp. Med. Biol. (1983) 160:3–13.
Kessel et al., Photo. Photo. Biol. (1987) 46:463–568.
Lipson et al., J. Natl. Cancer Inst. (1961) 26:1–8.
Morris, I. K. and Ward, D. A., Tetrahedron Letters (1988) 29(20): 2501–2504.

Primary Examiner—Richard L. Raymond
Attorney, Agent, or Firm—Irell & Manella

[57] ABSTRACT

Pure dimer and trimer compounds of hematoporphyrin are prepared and shown to be effective agents in photodynamic therapy. The compounds of the invention are of the formula

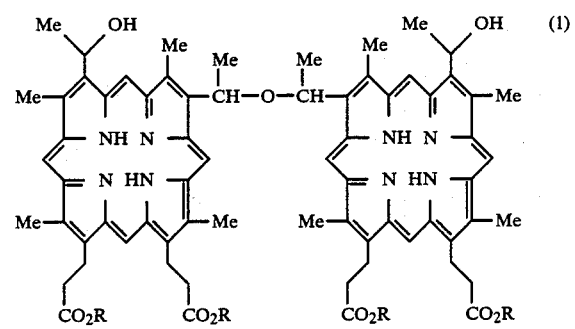

or

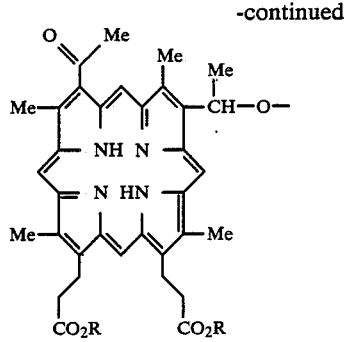

-continued

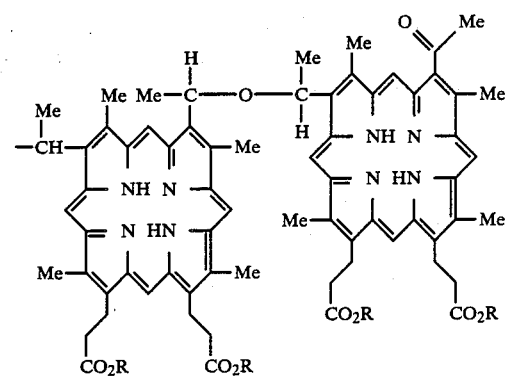

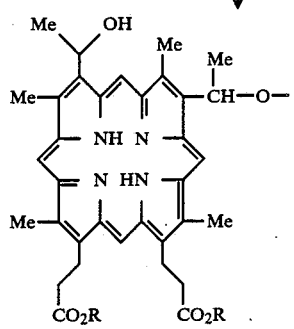

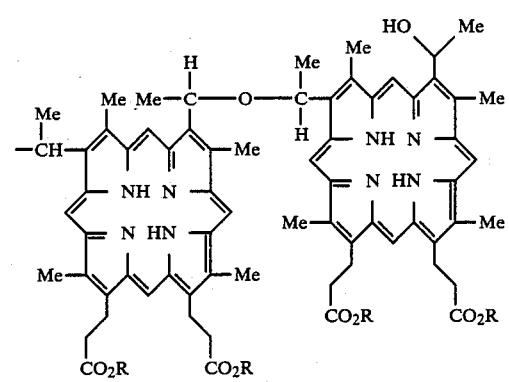

wherein each X is independently 1-hydroxyethyl or vinyl and wherein R is H or lower alkyl. The compounds of the invention can be conjugated to targeting substances such as immunoglobulins or to labels.

5 Claims, No Drawings

USE OF PURIFIED HEMATOPORPHYRIN TRIMERS IN PHOTODYNAMIC THERAPY

CROSS-REFERENCE TO RELATED APPLICATION

This is a continuation-in-part of U.S. patent application Ser. No. 215,592, filed 6 July 1988 and now pending.

TECHNICAL FIELD

The invention relates to the treatment of tumors using the process of photodynamic therapy (PDT). In particular, it concerns compounds useful in this treatment regime which are dimers or trimers of hematoporphyrin, and dehydrated forms thereof.

BACKGROUND ART

It has been known for some time that porphyrin related compounds accumulate at higher concentrations in tumor tissue as compared to some normal tissues, and that irradiation of these compounds using light of the proper wavelength results in an energized form which, upon decay, results in cytotoxicity. It is believed that excitation of the porphyrin or related material results in the formation of singlet oxygen which is in fact the toxic agent.

An extensive literature relating to the use of "hematoporphyrin derivative" (HPD) describes this process utilizing a preparation obtained when hematoporphyrin dichloride is treated using the procedure of Lipson, R. L., et al., *J National Cancer Inst* (1961) 26:1-8. More recently, it has been shown that if this hematoporphyrin derivative is treated at a suitable pH, aggregation occurs and the active material in the mixture can be prepared in crude form as a size segregated aggregate (see, for example, U.S. Pat. No. 4,649,151, incorporated herein by reference). This preparation is commercially available under the trademark Photofrin II.

It is clear that the preparation marketed as the Photofrin II composition is itself a mixture. It is known that the mixture contains porphyrins joined by ether linkages (Dougherty, T. J., et al., *Adv Exp Med Biol* (1983) 160:3-13), and more recently, Kessel, D., et al., *Photochem Photobiol* (1987) 46:463-568, has shown that ester linked porphyrins are contained in this mixture as well. Scourides, P. A., et al., *Cancer Res* (1987) 47 3439-3445 have synthesized an oligomeric mixture of ether linked porphyrins starting from hematoporphyrin dimethyl esters. The mixture was active in PDT, but was as complex a mixture as the Photofrin II preparation. Dimers of hematoporphyrin joined by ester linkages have also been prepared by Pandey, R. K., et al., *Cancer Res* (in press) and the dimers prepared were shown to be absent from the mixture in the Photofrin II composition as well as inactive in an in vitro assay.

Thus, it is known in the art that some elements of a mixture prepared when HPD is aggregated and segregated into higher molecular weight components are active in photodynamic therapy. However, it is not settled and not known what all of these active ingredients are, nor has it been possible to prepare single compound compositions which are useful in PDT. It would clearly be advantageous to utilize a purified and defined composition in this therapeutic method rather than a complex mixture, which while effective, is not completely understood.

DISCLOSURE OF THE INVENTION

The invention provides defined dimer and trimer conjugates of hematoporphyrin systems which are active and effective in PDT. Specifically, the invention provides dimers and trimers linked through ether linkages and obtained in isolated form.

Accordingly, in one aspect, the invention is directed to a compound of the formula

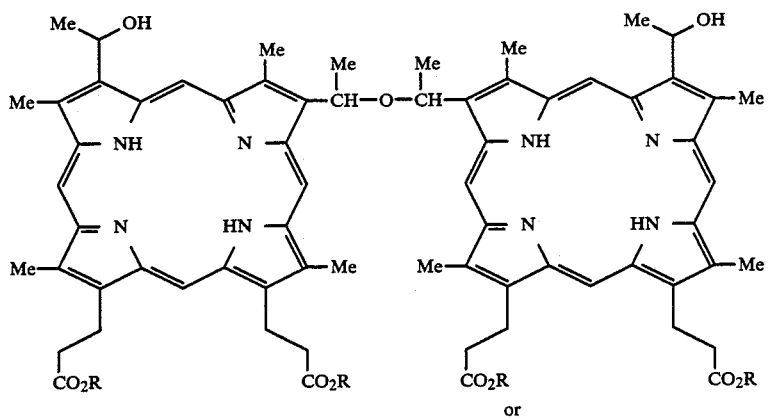

or

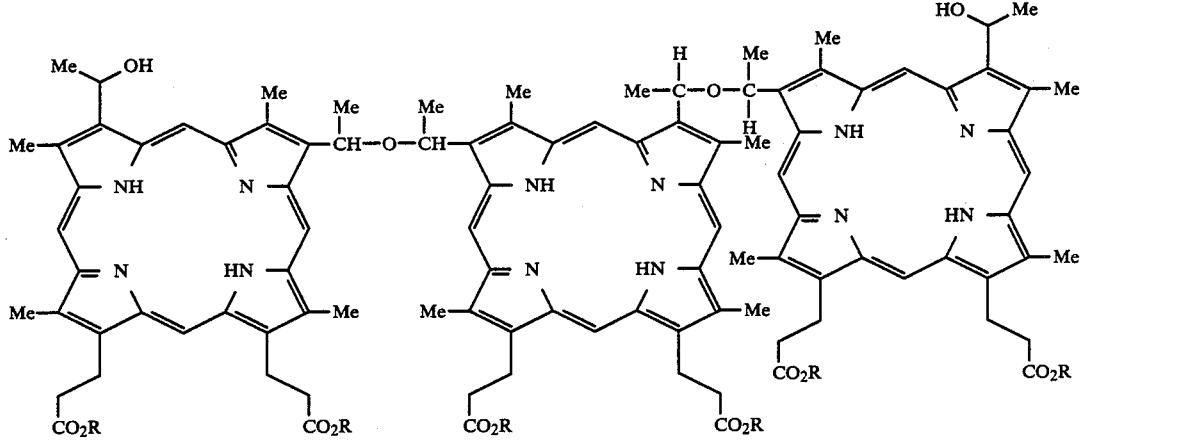

Formula (2)

wherein each X is independently CH₃CHOH— or CH₂=CH—, and wherein R is H or lower alkyl (C1–C4), said compound in purified and isolated form. The invention is also directed to pharmaceutical compositions in which one of the compounds above is an active ingredient and to methods of conducting photodynamic therapy using the compounds and compositions of the invention.

In another aspect, the invention is directed to the compounds of formulas (1) or (2) conjugated to a ligand which is capable of binding to a specific receptor such as an antibody or cellular receptor, and to compositions containing these conjugates and methods of conducting photodynamic therapy using the conjugates and their compositions.

MODES OF CARRYING OUT THE INVENTION

The invention provides a synthesis of pure compositions containing, in isolated form, the compounds of formula 1 or 2. Thus, by "isolated form" is meant that all of the porphyrin components of the composition have the same structural formula as shown in formula (1) or (2) or isomers of the structural formulas shown where the dimerization is effected through different combinations of A and B ring linkages. However, for those compounds which contain chiral centers, a mixture of stereoisomers is also included within the scope of the term "isolated form." These compositions of the invention may contain only one stereoisomer or several.

Furthermore, the compositions may contain only one or several A/B ring linkage isomers. As shown in formula (1), the ether linkage is between ring A of one porphyrin and ring A of the other. Linkage may also be A-B or B-B. Similarly, as shown in formula (2), linkage is A-A and B-A. It may also be a combination of B-A and B-B or B-A, or of B-B and B-A, or of A-A and B-B.

The compounds of the invention are synthesized using as starting material, 2,4-diacetyldeuteroporphyrin as the dialkyl ester. This compound is first partially reduced using a suitable reducing hydride, such as sodium borohydride, to obtain the corresponding alkyl diester of 4-acetyl-2-(1-hydroxyethyl)deuteroporphyrin-IX and its 2-acetyl-4-(1-hydroxyethyl)isomer. This mixture, one isomer of which is shown as formula (A), is used in further synthesis. The synthesis of the dimer of formula (1) is shown in Reaction Scheme 1.

Reaction Scheme 1

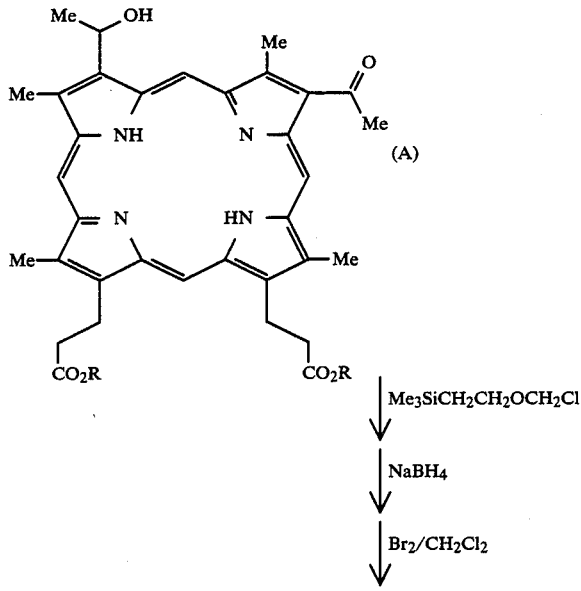

-continued
Reaction Scheme 1

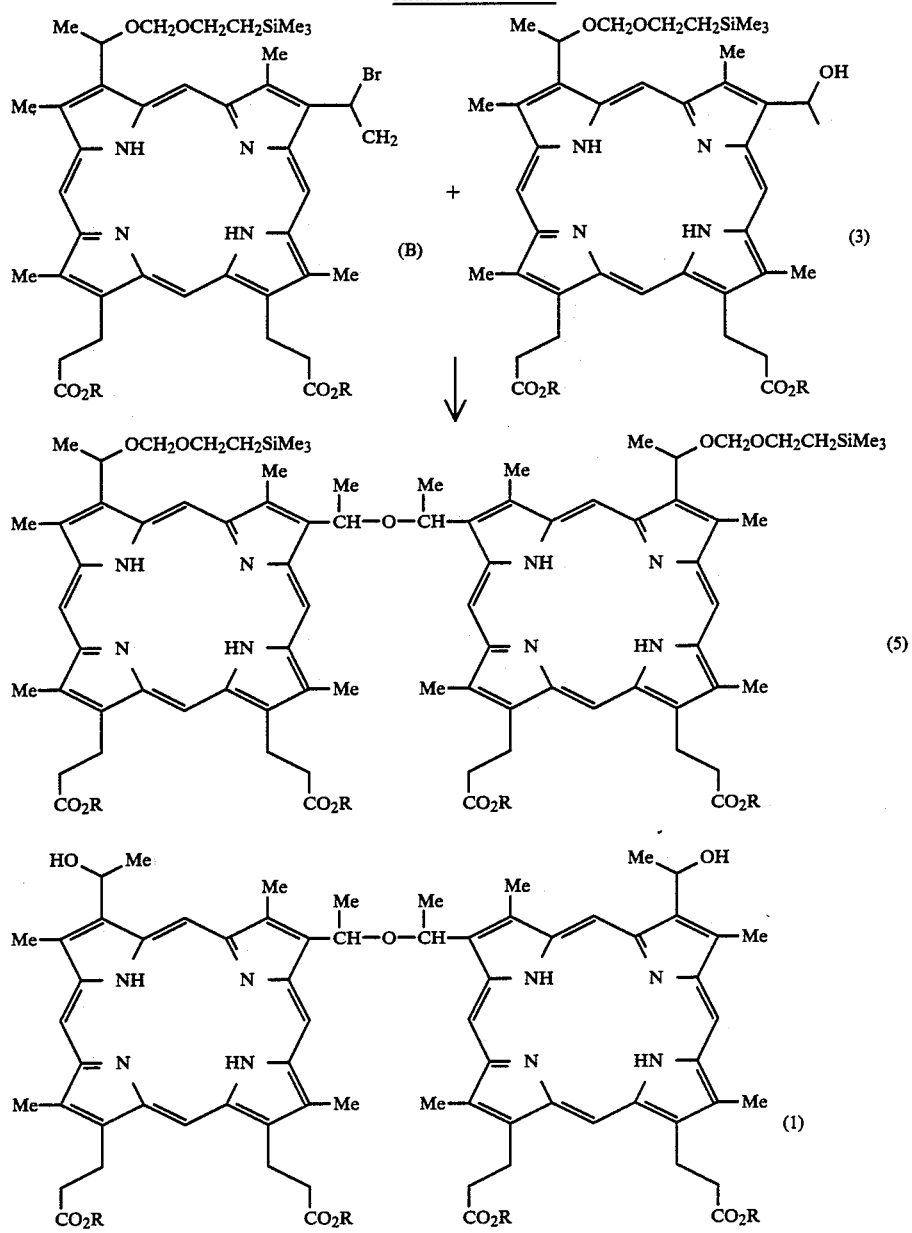

As shown, after protecting the hydroxyl group using a suitable protecting agent such as beta(trimethylsilyl)-ethoxymethyl chloride, reduction with a suitable hydride, such as sodium borohydride, effects the conversion of the remaining acetyl moiety to the corresponding alcohol and its corresponding 2,4-isomer.

Treatment with bromine in dichloromethane at a temperature of less than 40° results in the bromo derivative (B) which is not isolated. but is condensed after evaporation of the solvent, with compound (3) in dichloromethane to give the dimer of formula (5) Removal of the silyl protecting groups yields the desired compound of formula (1).

The dimer of formula (1) can also be synthesized using the scheme shown in Reaction Scheme 2.

Reaction Scheme 2

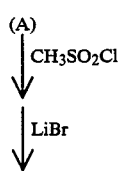

Reaction Scheme 2

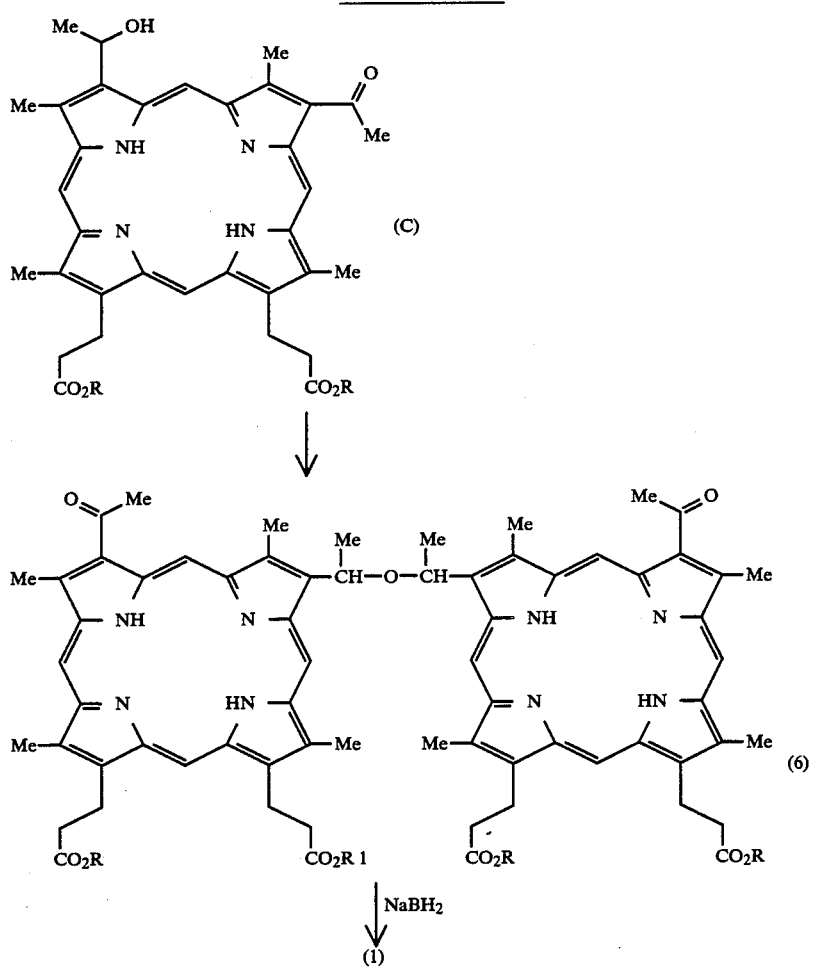

In this preparation, the 4-acetyl-2-(1-hydroxymethyl-deuteroporphyrin) dialkyl ester of formula (A) and its isomer are treated in dichloromethane with methane sulfonyl chloride at less than −70° C. under nitrogen for 1 hour, and then with lithium bromide to obtain the corresponding bromo derivative of formula (C) for condensation with the untreated porphyrin starting material of formula (A) to obtain the dimer of formula (6) which is then treated with sodium borohydride to obtain the desired dimer compound of formula (1).

Preparation of the trimer of formula (2) wherein both Xs are $CH_3CHOH-$ is shown in Reaction Scheme 3.

Reaction Scheme 3

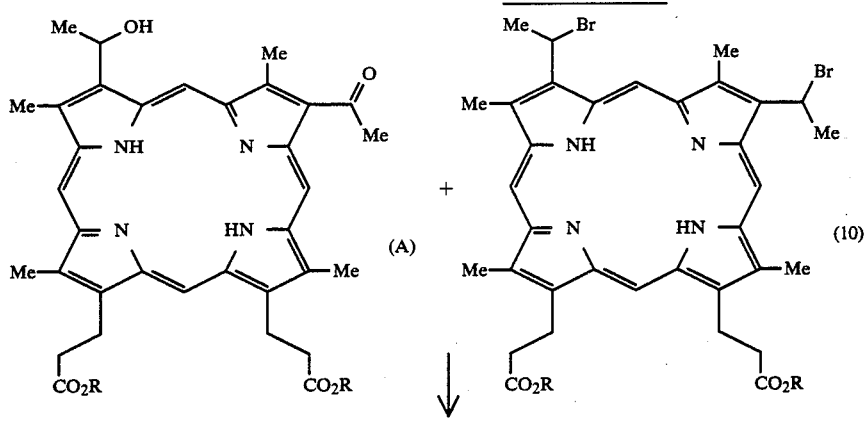

-continued
Reaction Scheme 3

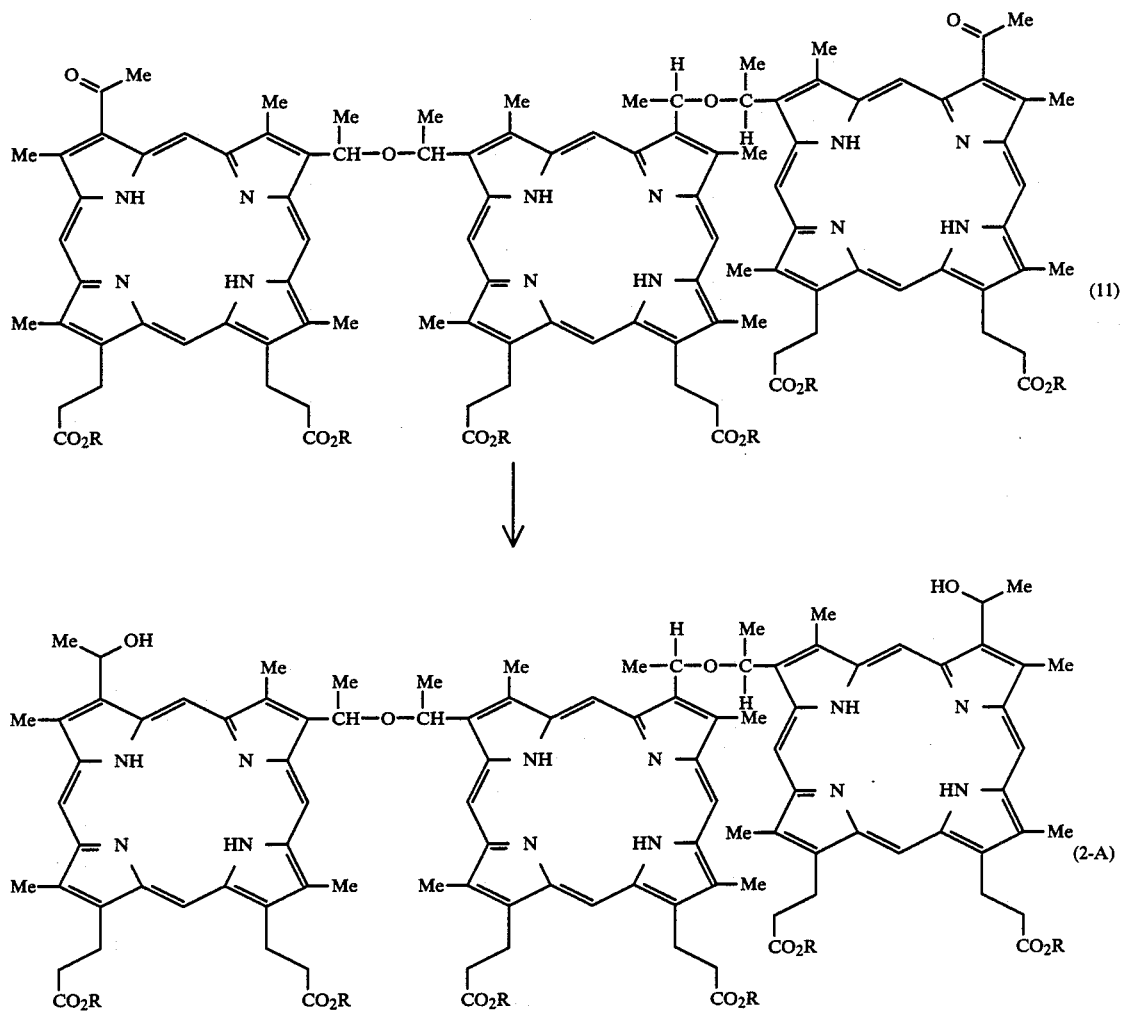

In this series of reactions, condensation of the porphyrin of formula (A) with the dibrominated form of hematoporphyrin of formula (10) results in the trimer of formula (11), which is the oxidized form of the desired compound of formula (2) Reduction of the compound of formula (11) with, for example, sodium borohydride, yields the desired trimer.

For preparation of the trimer of formula (2) wherein both Xs are vinyl, the reaction sequence is similar except that compound A is replaced by the commercially available material Hvd, which is a mixture of 2-(1-hydroxyethyl)-4-vinyl and 4-(1-hydroxyethyl)-2-vinyl deuteroporphyrin dimethyl ester. The remainder of the scheme is analogous, except that the last, reduction, step is unnecessary.

Similarly, for preparation of the embodiment of formula (2) wherein one X is vinyl and the other is 1-hydroxyethyl, an equimolar mixture of the compound of formula A and Hvd is used in the first condensation step. Reduction of the condensate is necessary to convert the acetyl substituent to 1-hydroxyethyl.

In all of the preparations above, either the compounds of the formulas shown or their A-B ring structural isomers or mixtures can be used. The formulas shown, therefore, are exemplary of all of these alternatives.

In all of the foregoing cases, also, the esterified carboxyl groups can be hydrolyzed using a 1:1 mixture of 1N sodium hydroxide and THF to obtain the corresponding dicarboxylic acids, or partially hydrolyzed to obtain the monocarboxylic acids.

The possibility of using compositions which consist essentially of the above-defined compounds as active ingredient make possible the derivatization of the dimer or trimer contained in order to provide a specific targeting mechanism. Commonly used target-specific components include monoclonal antibodies and ligands which bind to a cellular receptor. The compositions can also be conveniently labeled.

The target-specific component can then be, for example, an immunoglobulin or portion thereof or a ligand specific for a particular receptor. The immunoglobulin component can be any of a variety of materials. It may be derived from polyclonal or monoclonal antibody preparations and may contain whole antibodies or immunologically reactive fragments of these antibodies such as F(ab')$_2$, Fab, or Fab' fragments. Use of such immunologically reactive fragments as substitutes for whole antibodies is well known in the art. See, for example, Spiegelberg, H. L., in "Immunoassays in the Clinical Laboratory" (1978) 3:1-23.

Polyclonal anti-sera are prepared in conventional ways by injecting a suitable mammal with antigen to which antibody is desired, assaying the antibody level in serum against the antigen, and preparing anti-sera when the titers are high. Monoclonal antibody preparations may also be prepared conventionally such as by the method of Koehler and Milstein using peripheral blood lymphocytes or spleen cells from immunized animals and immortalizing these cells either by viral infection, by fusion with myelomas, or by other conventional procedures, and screening for production of the desired antibodies by isolated colonies. Formation of the fragments from either monoclonal or polyclonal preparations is effected by conventional means as described by Spiegelberg, H. L., supra.

Particularly useful antibodies include the monoclonal antibody preparation CAMAL1 which can be prepared as described by Malcolm, A., et al., *Ex Hematol* (1984) 12:539-547; polyclonal or monoclonal preparations of anti-M1 antibody as described by Mew, D., et al., *J Immunol* (1983) 130:1473-1477 (supra) and B16G antibody 1.20 which is prepared as described by Maier, T., et al., *J Immunol* (1983) 131:1843; Steele, J. K., et al., *Cell Immunol* (1984) 90:303.

The foregoing list is exemplary and certainly not limiting; once the target tissue is known, antibody specific for this tissue may be prepared by conventional means. Therefore the invention is applicable to effecting toxicity against any desired target.

The ligand specific for receptor, refers to a moiety which binds a receptor at cell surfaces, and thus contains contours and charge patterns which are complementary to those of the receptor. It is well understood that a wide variety of cell types have specific receptors designed to bind hormones, growth factors, or neurotransmitters. However, while these embodiments of ligands specific for receptor are known and understood, the phrase "ligand specific for receptor", as used herein, refers to any substance, natural or synthetic, which binds specifically to a receptor.

Examples of such ligands include the steroid hormones, such as progestrone, estrogens, androgens, and the adrenal cortical hormones; growth factors, such as epidermal growth factor, nerve growth factor, fibroblast growth factor, and so forth; other protein hormones, such as human growth hormone, parathyroid hormone, and so forth; and neurotransmitters, such as acetylcholine, serotonin, and dopamine. Any analog of these substances which succeeds in binding to the receptor is also included.

The conjugation of the target-cell-specific component to the dimers or timers can be effected by any convenient means. For proteins, such as Ig and certain receptor ligands, a direct covalent bond between these moieties may be effected, for example, using a dehydrating agent such as a carbodiimide. A particularly preferred method of covalently binding the dimers or trimers to the immunoglobulin moiety is treatment with 1-ethyl-3-(3-dimethylamino propyl) carbodiimide (EDCI) in the presence of a reaction medium consisting essentially of dimethyl sulfoxide (DMSO).

Of course, other dehydrating agents such as dicyclohexylcarbodiimide or diethylcarbodiimide could also be used as well as conventional aqueous and partially aqueous media.

Nonprotein receptor ligands can be conjugated to the dimers and trimers according to their relevant functional groups by means known in the art.

The active moieties of the conjugate may also be conjugated through linker compounds which are bifunctional, and are capable of covalently binding each of the two active components. A large variety of these linkers is commercially available, and a typical list would include those found, for example, in the catalog of the Pierce Chemical Co. These linkers are either homo- or heterobifunctional moieties and include functionalities capable of forming disulfides, amides, hydrazones, and a wide variety of other linkages.

Other linkers include polymers such as polyamines, polyethers, polyamine alcohols, derivatized to the components by means of ketones, acids, aldehydes, isocyanates, or a variety of other groups.

The techniques employed in conjugating the active moieties of the conjugate to the target-specific component include any standard means and the method for conjugation does not form part of the invention. Therefore, any effective technique known in the art to produce such conjugates falls within the scope of the invention, and the linker moiety is accordingly broadly defined only as being either a covalent bond or any linker moiety available in the art or derivable therefrom using standard techniques.

The dimer or trimer compounds per se or the conjugates may be further derivatized to a compound or ion which labels the drug. A wide variety of labeling moieties can be used, including radioisotopes and fluorescent labels. Radioisotope labeling is preferred, as it can be readily detected in vivo.

The compounds which are alone or are conjugates of dimer or trimer with a specific binding substance can be labeled with radioisotopes by coordination of a suitable radioactive cation in the porphyrin system. Useful cations include technetium and indium. In the conjugates, the specific binding substances can also be linked to label.

Administration and Use

The defined dimer and trimer compositions and their conjugates with target-specific substances of the invention are useful, in general, in the manner known in the art for hematoporphyrin derivative and for Photofrin II compositions. These compositions are useful in sensitizing neoplastic cells or other abnormal tissue to destruction by irradiation using visible light—upon photoactivation, the compositions have no direct effect, nor are they entered into any biological event; however the energy of photoactivation is believed to be transferred to endogenous oxygen to convert it to singlet oxygen. This singlet oxygen is thought to be responsible for the cytotoxic effect. In addition, the photoactivated forms of porphyrin fluorescence which fluoresce can aid in localizing the tumor. Thus, the dimer and trimer compounds of the invention are not consumed or altered in exerting their biological effects.

Typical indications, known in the art, include destruction of tumor tissue in solid tumors, dissolution of plaques in blood vessels (see, e.g., U.S. Pat. No. 4,512,762); treatment of topical conditions such as acne, athletes foot, warts, papilloma, and psoriasis and treatment of biological products (such as blood for transfusion) for infectious agents, since the presence of a membrane in such agents promotes the accumulation of the drug.

The compositions are formulated into pharmaceutical compositions for administration to the subject or applied to an in vitro target using techniques known in the art generally. A summary of such pharmaceutical compositions may be found, for example, in *Remington's Pharmaceutical Sciences*, Mack Publishing Co., Easton, Pennsylvania, latest edition. The compositions labeled or unlabeled, can be administered systemically, in particular by injection, or can be used topically.

Injection may be intravenous, subcutaneous, intramuscular, or, even intraperitoneal. Injectables can be prepared in conventional forms, either as liquid solutions or suspensions, solid form suitable for solution or suspension in liquid prior to injection, or as emulsions. Suitable excipients are, for example, water, saline, dextrose, glycerol and the like. Of course, these compositions may also contain minor amounts of nontoxic, auxiliary substances such as wetting or emulsifying agents, pH buffering agents and so forth.

Systemic administration can also be implemented through implantation of a slow release or sustained release system, by suppository, or, if properly formulated, orally. Formulations for these modes of administration are well known in the art, and a summary of such methods may be found, for example, in *Remington's Pharmaceutical Sciences* (supra).

If the treatment is to be localized, such as for the treatment of superficial tumors or skin disorders, the compositions may be topically administered using standard topical compositions involving lotions, suspensions, or pastes.

The quantity of dimer or trimer to be administered depends on the choice of active ingredient, the condition to be treated, the mode of administration, the individual subject, and the judgment of the practitioner. Depending on the specificity of the preparation, smaller or larger doses may be needed. For compositions which are highly specific to target tissue, such as those which comprise conjugates of the dimer or trimer with a highly specific monoclonal immunoglobulin preparation or specific receptor ligand, dosages in the range of 0.05-1 mg/kg are suggested. For compositions which are less specific to the target tissue, larger doses, up to 1-10 mg/kg may be needed. The foregoing ranges are merely suggestive, as the number of variables in regard to an individual treatment regime is large and considerable excursions from these recommended values are expected.

EXAMPLES

The following examples are intended to illustrate the invention but not to limit its scope.

EXAMPLE 1

Preparation of the Dimer

The method to prepare the dimer is generally that shown in Reaction Scheme 1. In this example, the dimethyl ester was used.

Thus, 4-acetyl-2-(1-hydroxyethyl)deuteroporphyrin IX dimethyl ester (A) and its 2-acetyl-4-(1-hydroxyethyl)isomer were prepared in 75% yield by partial reduction of 2,4-diacetyldeuterophorphyrin (Smith, K. M., et al., *J Am Chem Soc* (1983) 105:6638-6646) with sodium borohydride. The mixture was used as such for the entire synthesis of dimer (1) and the trimer (2). The hydroxyl group was then protected by treatment with beta(trimethylsilyl)-ethoxymethyl chloride (Lipshutz, B. H., et al., *Tetrahedron Lett* (1980) 21:3343-3346) and the resulting protected porphryin was isolated in 90% yield. Upon treatment with sodium borohydride, the reduced acetylated porphyrin was obtained in almost quantitative yield, and converted into the bromo derivative (B) by treatment with bromine in dichloromethane ($< -40°$ C. under an inert atmosphere). The bromo derivative was not isolated and after evaporation of the solvent it was condensed with porphyrin (3) in dichloromethane, to give the desired porphyrin dimer (5) in 32% yield, along with some protoporphyrin IX dimethyl ester. Problems were encountered in cleavage of the silyl groups using tetra-n-butyl ammonium fluoride at room temperature, and at higher temperatures only a small yield of (1) was obtained, along with large amounts of decomposition products.

EXAMPLE 2

Alternate Preparation of Dimer

In another approach, shown in Reaction Scheme 2, porphyrin (A), as a mixture of isomers, in dichloromethane was treated with methanesulfonyl chloride ($< -70°$ C. under nitrogen) for 1 hr. The mesylate so obtained was treated with lithium bromide (Corey, E. J., et al., *J Am Chem Soc* (1980) 102:1742-1744) under similar conditions used to synthesize the bromo derivative (C). The bromo derivative was not isolated, but was immediately condensed with porphryin (A) to produce the dimer (6) in 28% yield. [m/e 1232, 50%; 607, 10%; 307, 100%; $^1$H NMR, —CH(Me)O—, m, 6.6-6.9 ppm]. Treatment of (6) with sodium borohydride afforded the desired dimer (1) in quantitative yield as the (tetramethyl ester [m/e 1236, 100%; $^1$H NMR, —CH(Me)O—, m, 6.5-6.8 ppm]. The methyl esters were then hydrolyzed to the corresponding carboxylic acids (m/e 1180) by treatment with 1N sodium hydroxide in tetrahydrofuran.

EXAMPLE 3

Preparation of Trimer Wherein X is Hydroxyethyl

Along similar lines, diacetyl trimer (11) was synthesized in 31% yield by condensation of porphyrin (A) with (10) [m/e 1840, 100%; $^1$H NMR, —CH(Me)O—, m, 6.5-6.9 ppm], as shown in Reaction Scheme 3. Treatment of this trimer with sodium borohydride afforded the Hp trimer as the hexamethyl ester (2) in 98% yield, [m/e 1184, 100%; $^1$H NMR, —CH(Me)O—, m, 6.6-7.0 ppm], which, upon base hydrolysis, afforded the corresponding carboxylic acid, [m/e, 1760].

EXAMPLE 4

Synthesis of Trimer Wherein X is Vinyl

Protoporphyrin-9-dimethylester (15 mg) was treated with 30% HBr/acetic acid (2 ml) for 2 hr. The 2,4-(1-bromoethyl) derivative was dried under high vacuum and then condensed with Hvd (35 mg) dissolved in dry dichloromethane (10 mg) with stirring for 10 min at room temperature under a nitrogen atmosphere. The reaction mixture was poured into water and purified. The resulting compound of formula (2) wherein both Xs are vinyl was isolated in 32.6% (15 mg) yield along with Hp and Hvd as their methyl esters. MS: m/e 1809 (M+1, 20%) 1873 (Cu complex, M+2, 25%), 591 (100%). The results of HPLC showed three peaks due to the various positional derivatives.

EXAMPLE 5

Biological Testing

Biological testing was based on the standard system of subcutaneously implanted SMT-F tumor in DBA/2 mice. Tumors of 4.5–5.5 mm were exposed to 288 J/cm$^2$ of light from a filtered arc lamp (600–700 mm), 20–24 hr post i.p. injection of the test substance. The results of this test, are shown in Table 1 below.

TABLE 1

| | | Tumor Response | |
|---|---|---|---|
| | Dose | Response | |
| Compound | mg/kg | 1–2 days | 7 days |
| Photofrin ® II composition | 4.2 | 10/10 | 5/10 |
| Formula (1) | 4.2 | 0/10 | 0/10 |
| | 10.0 | 1/10 | 0/10 |
| | 5.0* | 7/10 | 2/10 |
| Formula (2) X=X===CH$_3$CHOH— | 4.2 | 5/10 | 3/10 |
| | 5.0 | 10/10 | 8/10 |
| Formula (2) X=X=CH$_2$=CH$_2$— | 6.0 | 9/9 | 9/9 |

*Treated after 3 hr.

As shown in Table 1, the hematoporphyrin dimer of formula (1) is only marginally active, while both trimer mixtures of positional isomers are as effect as the Photofrin ® II composition.

We claim:

1. A method to destroy or impair the functioning of target biological substrate which comprises contacting said target with an effective amount of a compound of the formula

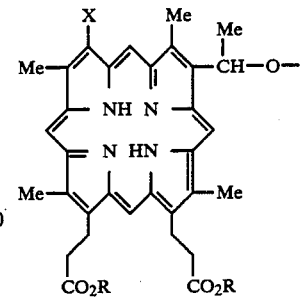

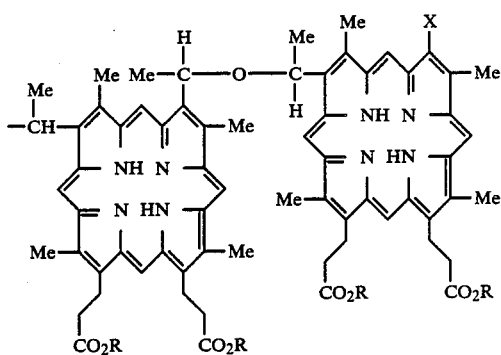

wherein each X is independently CH$_3$CHOH— or CH$_2$=CH— and wherein R is H or lower alkyl, or with a pharmaceutical composition thereof, and irradiating said target with light absorbed by said compound.

2. The method of claim 1 wherein one X is CH$_2$=CH— and the other is CH$_3$CHOH—.

3. The method of claim 1 wherein said pharmaceutical composition contains a mixture of compounds wherein X is CH$_3$CHOH— or CH$_2$=CH—.

4. The method of claim 1 wherein each X is CH$_3$CHOH—.

5. The method of claim 1 wherein each X is CH$_2$=CH.

* * * * *